United States Patent [19]
Methmanus-Spaltro

[11] Patent Number: 6,162,775
[45] Date of Patent: Dec. 19, 2000

[54] ANHYDROUS LIQUID COSMETIC COMPOSITIONS COMPRISING GLYCERIN AND POLYALKYLENE GLYCOL

[75] Inventor: Suree Methmanus-Spaltro, Bangkok, Thailand

[73] Assignee: Unilever Home & Personal Care USA, division of Conopco, Inc., Greenwich, Conn.

[21] Appl. No.: 09/373,273

[22] Filed: Aug. 12, 1999

[30] Foreign Application Priority Data

Aug. 14, 1998 [GB] United Kingdom ............ 9817817

[51] Int. Cl.⁷ ................ C11D 1/28; C11D 9/02; C11D 3/44

[52] U.S. Cl. ............. 510/130; 510/135; 510/141; 510/371; 510/396; 510/407; 510/414; 510/426; 510/429; 510/432; 510/490

[58] Field of Search .................. 510/130, 135, 510/141, 371, 396, 407, 414, 426, 429, 432, 490, 152, 437, 454, 481

[56] References Cited

U.S. PATENT DOCUMENTS

| | | | |
|---|---|---|---|
| 5,254,334 | 10/1993 | Ramirez et al. | 424/70 |
| 5,417,876 | 5/1995 | Tokosh et al. | 252/108 |
| 5,523,017 | 6/1996 | Moran et al. | 252/174.21 |
| 5,916,856 | 6/1999 | Massaro et al. | 510/141 |
| 5,945,389 | 8/1999 | Richard et al. | 510/153 |

FOREIGN PATENT DOCUMENTS

| | | |
|---|---|---|
| 0027730 | 4/1981 | European Pat. Off. . |
| 0261754 | 3/1988 | European Pat. Off. . |
| 0586929 | 3/1994 | European Pat. Off. . |
| 196 24 870 | 1/1998 | Germany . |
| 4-264186 | 9/1992 | Japan . |
| 9-272894 | 10/1997 | Japan . |
| 1357000 | 6/1974 | United Kingdom . |

*Primary Examiner*—Yogendra Gupta
*Assistant Examiner*—Charles Boyer
*Attorney, Agent, or Firm*—Ronald A. Koatz

[57] ABSTRACT

An anhydrous foaming cleansing composition for topical application to the human skin, comprising an anionic surfactant, glycerine, polyethylene glycol, and a water insoluble benefit agent.

12 Claims, No Drawings

ANHYDROUS LIQUID COSMETIC COMPOSITIONS COMPRISING GLYCERIN AND POLYALKYLENE GLYCOL

This invention relates to cosmetic applications for topical applications to the human skin. In particular, it relates to anhydrous cosmetic compositions, with the capacity for self warming on application.

Anhydrous cosmetic compositions which provide a warming benefit on application are as such known. For example, EP-A-27730 (Johnson Company) describes a cosmetic composition, which may for example be a hair treatment or hand treatment composition, which generates heat on contact with water. In this application, heat generation is alleged to be provided by the presence of polyethylene oxides, polypropylene oxides, and derivatives thereof, and a 2 to 9 carbon atom alkaline glycol. However, we have found that the formulation of compositions based on or containing significant amounts of propylene glycol needs to be very carefully controlled, since a number of propylene glycol based compositions suffer from product separation on storage.

In terms of further teachings in the field, EP-A-586929 (Kao) describes a two pack system which generates heat on the addition of water, and produces a physiologically compatible salt that generates heat on mixture with water. Also contributing to the heat felt by the user on hydration of the product is the heat of hydration of polyethylene glycol.

Further, GB-A-1357000 (British American Tobacco Company) describes a topical cosmetic composition comprising an anhydrous polyol and an absorbent particulate filler material. Suitable polyols are said to include propylene glycol, glycerol, 1,3 butylene glycol, and polyethylene glycols having an average molecular weight of from 2 to 300 and from 1000 to 6000.

We have found that a particularly suitable cosmetic composition can be prepared for topical application, which composition is self heating, has good mildness and foaming properties, and which has further benefits not appreciated in the prior art.

Thus, according to a first aspect of the invention, there is provided an anhydrous foaming cleansing composition for topical application to the human skin, comprising an anionic surfactant, glycerine, polyethylene glycol, and a water insoluble benefit agent.

The surfactant contained in the composition may be any combination of surfactants, provided that it comprises an anionic surfactant and it provides the composition with a suitable level of foaming and mildness. As such, the surfactant component of the composition may comprise in addition to anionic surfactants soaps, cationic, nonionic, zwitterionic and amphoteric surfactants, and mixtures thereof.

Suitable soaps include these having carbon chain lengths of $C_8$–$C_{24}$, be saturated or unsaturated, and have any appropriate cation, such as sodium, potassium, ammonium or triethylammonium.

The composition according to the invention comprises an anionic surfactant, which is preferably chosen from alkyl sulphates, alkyl ether sulphates, alkyl sulphonates, alkyl aryl sulphonates, olefin sulphonates, acyl sarcosinates, acyl taurides, acyl isethionates, nonoalkyl sulphosuccinates, diallylsulphosuccinates, N-acylated α-amino acids, alkyl carboxylates, monoalkyl phosphates and dialkyl phosphates, and mixtures thereof. Specific examples of suitable anionic surfactants include:

alkyl sulphates, such as sodium lauryl sulphate [eg EMPICOL CX available from Albright and Wilson], and triethanolaminde lauryl sulphate [eg EMPICOL TL40/T, available from Albright and Wilson].

alkylether sulphates, such as sodium lauryl ether sulphate [eg EMPICOL ESB70, available from Albright and Wilson].

alkyl sulphonates, such as sodium alkane ($C_{13-18}$) sulphonate [eg HOSTAPUR SAS 30, available from Hoechst].

alkylaryl sulphonates, such as sodium alkyl benzene sulphonate [eg TEEPOL CM44, available from Shell].

olefin sulphonates, such as sodium olefin sulphonate ($C_{5-18}$) [eg HOSTAPUR OS, available from Hoechst].

acyl sarcosinates, having the structure: (51)

where $R^3$ is chosen from $C_{6-14}$ alkyl, and
M is a counterion chosen from alkali metals, ammonium and substituted ammonium such as alkanolammonium.

An example of an acyl sarcosinate having the structure (51), is sodium lauryl sarcosinate [eg HAMPSOYL L-95, available from Grace].

acyl taurides, having the structure (52):

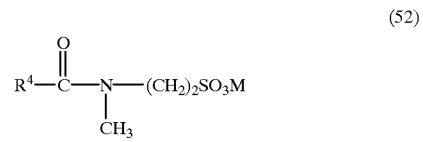

wherein $R^4$ is chosen from $C_{8-18}$ alkyl

An example of an acyl tauride having the structure (52) is coconut methyl taurine [eg FENOPEN TC 42, available from International Specialty Products].

acyl isethionates, having the structure (53):

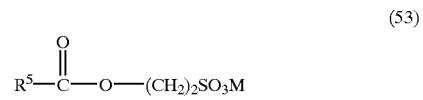

wherein $R^5$ is chosen from $C_{8-18}$ alkyl.

An example of an acyl isethionate having the structure (53) is sodium acyl isethionate [eg JORDAPON C1, available from Jordon).

monoalkyl sulphosuccinates, having the structure (54):

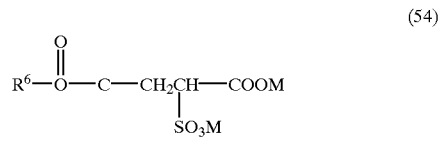

where $R^6$ is chosen from $C_{10-20}$ alkyl.

Examples of monoalkyl sulphosuccinates having the structure (54) include:

sodium lauryl sulphosuccinate [eg EMPICOL SLL, available from Albright and Wilson].

magnesium alkyl sulphosuccinate [eg ELFANOL 616 Mg, available from Akzo].

sodium lauryl ethoxysulphosuccinate [eg EMPICOL SDD, available from Albright and Wilson].

coconut monoethanolamide ethoxysulphosuccinate [eg EMPICOL SGG].

disodium lauryl polyglycolether sulphosuccinate [eg SURTAGENE S30, available from CHEM-Y].

polyethyleneglycol sulphosuccinate [eg REWOPOL SBFA 30, available from REWO].

dialkyl sulphosuccinates, having the structure (55):

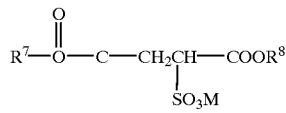

(55)

where $R^7$ and $R^8$ are the same or different, and are chosen from $C_{6-14}$ alkyl.

An example of a dialkyl sulphosucciante having the structure (55) is sodium dilauryl sulphosuccinate [eg EMCOL 4500, available from Witco].

N-acylated α-amino acids, such as sodium lauroyl glutamate [eg ACYLGLUTAMTATE LS- 1, available from Ajinomoto Co Inc].

alkyl ether carboxylates, such as $C_{12-14}O(EO)_4OCH_2CO_2Na$ [eg AKYPO RLM 38, available from Akzo].

monoalkyl phospates and dialkyl phospates, such as dioctyl phosphate.

Further examples of anionic surfactants (and of the other types of surfactants) are described in "Surface Active Agents and Detergents" (vols. I and II), by Schwartz, Ferry and Bergh.

In certain embodiments, preferred anionic surfactants include alkyl ether sulphates, fatty acid soaps, allkyl sulphates, alkyl sulponates, isethionic acid derivatives, and mixtures thereof. In certain embodiments, preferred non-soap anionic surfactants may be $C_8$–$C_{22}$ alkyl unsubstituted isethionates.

The composition of the invention can also comprise a cationic surfactant. Suitable cationic surfactants are those with the structure (57):

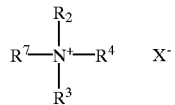

(57)

where $R^1$, $R^2$, $R^3$ and $R^4$ each represents alkyl or aryl groups,
and X represents a halogen counterion.

Preferred cationic surfactants in accordance with structure (57) include:

Hexadecyl trimethyl ammonium chloride, such as Arquad 16, available from Akzo.

Dihydrogenated tallow dimethyl ammonium chloride, such as Arquade 2HT, available from Akzo.

Dodecyl benzyl dimethyl ammonium bromide, such as Amoxyl Br1244, available from Seppic.

Cocoamidopropyl trimethyl ammonium chloride, such as Empigen CSC, available from Albright and Wilson.

The composition of the invention can also comprise an amphoteric surfactant. Suitable amphoteric surfactants are derivatives of aliphatic quaternary ammonium, phosphonium and sulphonium compounds, wherein the aliphatic radicals contain from 8 to 18 carbon atoms, and may be straight chain or branched, and further contain an anionic water solubilising group, such as carboxyl, sulphonate, sulphate, phospate or phosphonate.

Preferred-amphoteric surfactants include:

Alkyl betaines, having the structure (58):

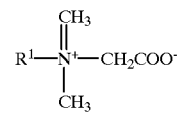

(51)

where $R^1$ is $C_{1-16}$ alkyl.

An example of an alkyl betaine having the structure (58) is lauryldimethyl betain [eg EMPIGEN BB, available from Albright and Wilson].

Alkylamidopropyl betaines, having the structure (59):

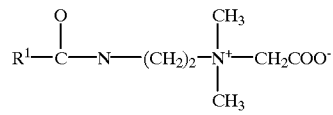

(59)

An example of an alkylamidopropyl betaine having the structure (59) is cocamidopropyl betaine [eg TEGOBETAIN L7, available from Goldschmidt).

Alkylamphoglycinates or Alkylamphopropionates having the structure (60):

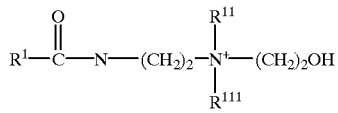

(60)

where $R^{11}$ is chosen from H, $CH_2COO$ and $(CH_2)_2COO$, and $R^{111}$ is chosen from $CH_2COO$ and $(CH_2)_2COO$ Suitable examples of compounds (60) are cocoamphoglycinate (available from International Specialty Products), and cocoamphopropionate.

Sultaines, having the structure (61):

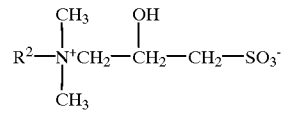

(61)

where $R^2$ is chosen from $C_{12-16}$ alkyl alkylamido groups.

An example of a sultaine having the structure (61) is cocamidopropylhydroxysultaine [eg CYCLOTERIC BET-CS, available from Alcolac).

The most preferred amphoteric surfactants are lauryl dimethyl betaine and cocamidopropyl betaine.

Such amphoteric surfactants can contribute to the foaming of the skin cleansing composition, while ameliorating the harshness of the anionic surfactant.

The composition of the invention can also comprise a nonionic surfactant. Suitable nonionic surfactants include polyoxyethylene allyl esters, polyoxyethylene alkyl ethers, and alkyl polyglycosides.

A suitable example of a polyoxyethylene alkyl esters is that having the CTFA designation Polysorbate 80 which is a mixture of oleate esters of sorbitol and sorbitol anhydrides, condensed with approximately 20 moles of ethylene exodie. Also suitable is Polysorbate 20 which is a mixture of laurate esters or sorbitol and sorbitol anhydrides condensed with approximately 20 moles of ethylene oxide.

Polysorbate 80 and Polysorbate 20 are available commercially as TWEEN 80 and TWEEN 20 respectively, from ICI Americas.

Also suitable for use in the compositions of the invention is the polyethylene glycol ether of $C_{9-11}$ alcohol with an average of 8 ethoxy units, which is available commercially as NONIDET LE-8T or as SYNPERIONIC 91-8T, and the polyethylene glycol ether of $C_{12-15}$ alcohol with an average of 9 ethoxy units which is available commercially as DOBANOL 25-9.

Particularly useful alkyl polyglycosides include the glycosides of glucose or glucose oligomers where the alkyl chain can be $C_{8-16}$ and the average number of glucose units is 1 to 2. A suitable example is ORAMIX NS 10 which is the glucoside of $C_{10-12}$ fatty alcohol with an average of about 1.5 glucose units.

Conveniently the surfactant is present in the composition at a level of 5–50% by weight. Preferably the level of surfactant in the composition is at least 10% by weight; preferably, the level of surfactant in the composition is less than 35% by weight. The anionic component of the surfactant content of the composition can typically be 40–100% of the total surfactant content of the composition.

In a preferred embodiment, the composition may contain at least 5%, more preferably at least 8% by weight, even more preferably at least 10% by weight of sodium cocoyl isethionate surfactant. In such compositions, a distinct improvement in sensory properties of the composition was perceived.

Conveniently, the blend of surfactants in compositions according to the invention is selected so as to enhance the lather volume and rinsability of the composition.

Preferably, the polyethylene glycols used in compositions according to the invention is a blend of polyethylene glycols having a variety of molecular weights; preferably, at least 50% of the polyethylene glycol blend used in compositions according to the invention has a molecular weight of less than 600, conveniently in the molecular weight of 200–600. However, higher molecular weight polyethylene glycols can usefully be used in the composition provided that they are soluble in the formulation.

Conveniently, the polyethylene glycol used in the composition have a molecular weight of less than 5,000; preferably 95% or more of the polyethylene glycols in the composition have a molecular weight of less than this.

Compositions according to the invention have been found to have particularly beneficial properties, in terms of their self heating properties on exposure to water, but also in relation to their stability. Further, cosmetic compositions according to the invention which comprise the blend of glycerine and polyethylene glycol components have been found to be particularly suitable for delivery of components which are not soluble in water, and which may otherwise be difficult to deliver from an aqueous based composition. As such, compositions according to the invention have been found to be particularly suitable for delivery of these components.

Other benefits which may be attained with compositions according to the invention include the provision of soft radiant skin after use, reduced skin oiliness, moisturization and mildness, as well as good rinsability.

An essential component of the composition is glycerine. Preferably, glycerine is present at a level of 5% to 25%, more preferably 10% to 20% by weight of the composition.

A further essential component of the composition is a blend of polyethylene glycols, which preferably comprise of at least 50% by weight of the polyethylene glycol component of polyethylene glycols having a molecular weight of 600 or less. The polyethylene glycol component of the composition may also comprise other, high molecular weight polyethylene glycols, which may typically have a molecular weight up to about 6000. Preferably, the polyethylene glycol component of the composition comprises from 20% to 70% by weight, more preferably from 25% to 50% by weight of the composition.

Compositions according to the invention are anhydrous; that is they contain a maximum of 1% by weight of water.

In certain embodiments, a preferred optional component is propylene glycol, though the level of propylene glycol is carefully controlled, since excessive levels of propylene glycol may prejudice the stability of the composition. Suitable levels of propylene glycol are typically 0.2–15%, more typically 1–13% by weight of the composition.

As referred to above, compositions according to the invention may be particularly suitable for the delivery of water insoluble components. Such components include but are not limited to benefit agents such as skin soothing agents, refreshing agents, healing agents, cooling agents, toning agents, blood flow promoting agents, anti-inflammatory agents, moisturising agents, anti-ageing agents, and sunscreen agents. A specific example of a suitable sunscreen agent is Parsol MCX.

An advantage of compositions according to the invention is that they may facilitate the solubilization and/or delivery of components which are difficult to deliver from aqueous based compositions, and may be considered insoluble in aqueous compositions. Typically, such benefit agents may be present at levels of up to 20%, more peferably 0.1–10%, even more preferably 0.5–8% by weight.

The product can take any convenient product form, and is preferably a liquid product. Conveniently, the product can be a facial foam or a shower cream. Conveniently the composition is not encapsulated, but is a free flowing liquid.

Products according to the invention have been found to provide suitable skin warming on application, which causes the pores in the skin to open more widely, and thus promote deeper cleansing.

The invention will now be described by way of example only, with reference to the following examples.

EXMAPLE 1

The following composition provided a suitable self warming facial foam composition according to the invention.

| Component | % | Tradename | Supplier |
|---|---|---|---|
| Propylene glycol | 13.0 | propylene glycol | Dow Chemicals |
| Glycerine | 14.0 | glycerol | GBT |
| Potassium laurate/myristrate/stearate | 22.0 | Nonsoul LK-2 MK1/SK-1 | NOF Corp |
| PEG 300/400/600 | 29.0 | Carbowax 300-600 | Union Carbide |
| PEG 60000 Distearate | 3.0 | Nionion DS-60HN | Nippon Oils & Fats |
| Ethylene glycol monostearate | 8.0 | Cutina EGMS | Henkel |
| Oleyl alcohol 20 mole ethyoxylate | 5.5 | Rhodasurf ON-870 | Rhone Poulent |

-continued

| Component | % | Tradename | Supplier |
|---|---|---|---|
| Stearic acid | 1.0 | Pristerene 4900 | Unichema |
| Sedaplant extract | 1.0 | Sedaplant Richter | Chemisches Laboratorium Dr Kurt Richter GmbH |
| Minor ingredients (perfume, etc.) | to 100.0 | | |

EXAMPLE 2

The following composition provided a suitable self warming facial foam composition according to the invention.

| Component | % | Tradename | Supplier |
|---|---|---|---|
| Propylene glycol | 13.0 | Propylene Glycol | Dow Chemicals |
| Glycerine | 16.0 | Glycerol | LBT |
| Potassium laurate | 7.0 | Nonsoul LK-2 | NAF Corp. |
| Sodium cocoyl isethionate | 11.0 | Elfan AT 84G | Akzo |
| PEG 300/400/600 | 29.0 | Carbowax 300/400/600 | Union Carbide |
| PEG 6000 Distearate | 3.0 | Nionion DS-60HN | Nippon Oil & Fats |
| Ethylene glycol monostearate | 8.0 | Cutina EGMS | Henkel |
| Oleyl alcohol 20 mole ethoxylate | 6.0 | Rhodasurf ON-870 | Rhone Poulenc |
| Stearic acid | 1.1 | Pristerine 4900 | Unichema |
| Sedaplant extract | 1.0 | Sedaplant Richter | Chemisches Laboratorium Dr Kurt Richter GmbH |
| Minor ingredients (perfume, etc.) | to 100 | | |

What is claimed is:

1. A liquid anhydrous foaming cleansing composition for topical application to the human skin, comprising:
   (1) an anionic surfactant selected from the group consisting of potassium soaps, a $C_8$–$C_{22}$ alkyl unsubstituted isethionate and mixtures thereof;
   (2) 5 to 25% by wt. of composition glycerin;
   (3) 20 to 70% by wt. of composition polyethylene glycol; and
   (4) a water insoluble benefit agent.

2. A cleansing composition according to claim 1, comprising at least 5% of sodium cocoyl isethionate.

3. A cleansing composition according to claim 1, wherein the surfactant comprises 5–50% by weight of the composition.

4. A cleansing composition according to claim 3, wherein the composition comprises at least 10% by weight of surfactant.

5. A cleansing composition according to claim 1, wherein the anionic surfactant comprises 40–100% by weight of the surfactants in the composition.

6. A cleansing composition according to claim 1, wherein at least 50% by weight of the polyethylene glycol in the composition has a molecular weight of 200–600.

7. A cleansing composition according to claim 1, wherein the polyethylene glycol in the composition has a molecular weight of less than 5,000.

8. A cleansing composition according to claim 1, wherein the composition contains less than 1% by weight water.

9. A cleansing composition according to claim 1, wherein the composition additionally comprises 0.2–15% by weight propylene glycol.

10. A cleansing composition according to claim 1, wherein the composition additionally comprises an amphoteric surfactant.

11. A cleansing composition according to claim 10, wherein the amphoteric surfactant comprises at least 5% by weight of the composition.

12. A cleansing composition according to claim 1, wherein the benefit agent is selected from as skin soothing agents, refreshing agents, healing agents, cooling agents, toning agents, blood flow promoting agents, anti-inflammatory agents, moisturising agents, anti-ageing agents, and sunscreen agents.

* * * * *